United States Patent [19]

Hansen et al.

[11] 4,261,372

[45] Apr. 14, 1981

[54] ELECTRODE FOR IMPLANTATION INTO COCHLEA

[76] Inventors: Carl C. Hansen, Sadolinsgade 114 B, DK-5000 Odnese; Ole M. Lauridsen, Kaervej 13, DK-3520 Farum, both of Denmark

[21] Appl. No.: 959,757

[22] Filed: Nov. 13, 1978

[30] Foreign Application Priority Data

Nov. 22, 1977 [DK] Denmark ............................. 5165/77

[51] Int. Cl.$^3$ ............................................... A61N 1/04
[52] U.S. Cl. .................................. 128/784; 179/107 R
[58] Field of Search ............................ 128/784–789, 128/799, 802, 419 R, 639, 642, 1 R; 179/107 R, 107 E

[56] References Cited

U.S. PATENT DOCUMENTS

| | | | |
|---|---|---|---|
| 3,253,595 | 5/1966 | Murphy, Jr. et al. | 128/785 |
| 3,449,768 | 6/1969 | Doyle | 128/1 R X |
| 3,751,605 | 8/1973 | Michelson | 179/107 R |
| 3,752,939 | 8/1973 | Bartz | 179/107 R |
| 3,788,329 | 1/1974 | Friedman | 128/786 |
| 3,866,615 | 2/1975 | Hewson | 128/784 X |
| 4,063,048 | 12/1977 | Kissich, Jr. | 179/107 R |

OTHER PUBLICATIONS

Sonn et al., "A Prototype Flexible Microelectrode Array...", Med. & Biol. Eng., Nov. 1974, pp. 778–790.
Prohaska, "A Multielectrode for Intracortical Recordings...", EEG & Clin. Neuro., 1977, 42, No. 3, 421–422.
Gheewala et al., "A CMOS... Stimulator for the Deaf", IEEE J. Solid State Circuits, vol. 10, No. 6, pp. 472–479, Dec. 1975.

*Primary Examiner*—Lee S. Cohen
*Attorney, Agent, or Firm*—LeBlanc, Nolan, Shur & Nies

[57] ABSTRACT

An electrode in the form of a foil-like flexible, electrically insulating support member having nerve electrodes supported thereupon for implantation into the cochlea. The electrode establishes electrical communication to the acoustic nerves of the human ear, substantially in the area of the cochlea containing the auditory nerves pertaining to that part of the audible spectrum, which is relevant to the intelligibility of speech. The electrode is provided with two prongs and a shank, each prong having a length which corresponds to the length of the turn in the cochlea into which it is to be inserted during implantation and hence the two prongs are of different lengths. Further, each prong terminates in a bevelled pilot guiding member which guides each prong through its respective turn in the cochlea to thereby reduce damage to the auditory nerves. During implantation each prong passes through only a single turn of the cochlea and is prevented from gouging into the walls of the cochlea due to provision of the bevelled guiding member. The guiding member can be provided as a drop-shaped member secured to the end of each prong or by forming an eyelet in the distal ends of the prongs.

4 Claims, 4 Drawing Figures

ELECTRODE FOR IMPLANTATION INTO COCHLEA

The present invention is related to an electrode for implantation into the cochlea in order to establish electrical communication to the acoustic nerves of the human ear, the electrode comprising an insulating support member having nerve contact points and associated supply lines.

Electrodes of this kind have been described by Martin Sonn and Wolfgang Feist in an article entitled "A prototype flexible microelectrode array for implant-prosthesis applications" in *Medical and Biological Engineering*, Nov. 1974, pages 778–790 and are illustrated in FIG. 1. This prior art electrode is disposed to be inserted through an aperture in a turn of a patient's cochlea, whose internal ear is defective, in order to establish communication substantially in the area of cochlea containing the acoustic nerves pertaining to that part of the audible spectrum, which is relevant to the intelligibility of speech. Accordingly it has such an extension that it has to be introduced into about nearly two turns of cochlea. It has appeared, however, that a satisfactory result was not attained, in as much as it has certainly been possible to bring the patent to such a condition that she or he could interpret electrical signals supplied through the electrode as being sound but not as being intelligible speech. The present invention is based on the opinion that this fact is due to damaging of the patient's acoustic nerves during the insertion of the electrode into the cochlea. Accordingly, it is an object of the present invention to provide an improved embodiment of an electrode of the kind discussed above, by means of which the damage of the acoustic nerves during the implantation can be avoided.

The present invention is based on the acknowledgement, that the entire area of cochlea which is relevant to speech cannot be contacted collectively, because an electrode having a sufficient extension for this purpose will act unavoidably as a chisel, which during the introduction gouges into cochlea and in this way damages the interior walls of cochlea and possibly the acoustic nerves too. Consequently it would be obvious to implant a number of shorter electrodes, but this will cause difficulties in practice. Partly, implantation of a number of electrodes would last a longer time than it would be permitted to keep the lymph-filled cochlea open and partly the attachment of a number of electrode ends or connection of lines to an external signal source would cause further difficulties compared to application of only a single electrode.

SUMMARY OF THE INVENTION

According to the present invention the draw-backs of the prior art electrode are obviated by designing the electrode as a fork having two prongs and a shank, each prong having a length, which corresponds essentially to the length of the turn in the cochlea, into which it is to be introduced and by each prong terminating in a bevelled guiding surface.

An electrode of this design permits substantially safer contact-making because the prongs are of shorter length, which are to be introduced through individual openings to the cochlea, now have to pass through only a single turn of the cochlea and during this introduction are prevented from cutting into the walls of cochlea due to the presence of the bevelled guiding surface. This reduced tendency of damaging the walls of cochlea is further increased thereby that the prongs now have to pass through only a single turn in cochlea and not as previously through two turns. Hence, the discussed chisel effect can be avoided and additionally, the two integral prongs are substantially easier to control or guide during the surgical operation. Further it is achieved, that the attachment of the contact points for both of the prongs can be done by securing the intermediate piece between the prongs and the shank, for example to the stapes in the middle ear. The last mentioned possibility would not exist in connection with two separate electrodes.

An embodiment of the electrode according to the invention is characterized in that the bevelled guiding surface is made up of an attached, for instance drop-shaped, pilot member. Thereby the advantage is in providing a pilot member which has a substantially hemispherical end surface, which effectively guides the prong through the particular turns in the cochlea.

In a modified embodiment of the electrode according to the invention the bevelled guiding surface is made up by bending the outermost end of the insulating support member. In this manner the manufacture of the electrode is facilitated and its weight is decreased which may be valuable when inserting the electrode into the cochlea.

The invention will now be described below in further details having reference to the accompanying drawing, in which FIG. 1 illustrates an embodiment of a prior art electrode, FIG. 2 illustrates a first embodiment of an electrode according to the invention, FIG. 3 is an enlarged, sectional view of a detail from the electrode shown in FIG. 2, and FIG. 4 is a sectional view of another embodiment of an electrode according to the invention.

DESCRIPTION OF THE PREFERRED EMBODIMENTS

Figure 1:
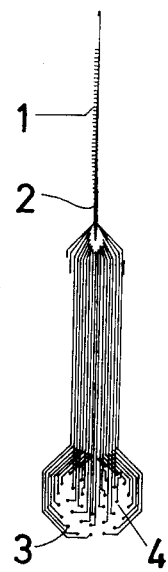

The prior art electrode illustrated in FIG. 1 comprises an insulating, supporting foil member, onto which a plurality of nerve electrodes 1 are attached, each electrode being connected through individual, mutually insulated conductors 2 to an individual connecting point 3 in a socket member 4. All materials have to be selected with regard to be inert to body tissue and fluids. On the drawing the conductors look like a single conductor, because this prior art electrode has printed circuit connections on either side. The length of the part of the electrode being provided with nerve electrodes 1 corresponds to the length of the parts of the cochlea's inner turns—it has in total two and a half turns—which include that part of the basilar membrane, which corresponds to the frequencies being of importance for the capability of hearing speech. It is a length, which corresponds to approximately two turns of the cochlea.

It will be understood that if from outside and through the cranium there is provided an opening in cochlea for insertion of an electrode and attempts are made to insert an electrode of the kind illustrated, and it is expected that such an electrode will wind itself through approximately two succeeding turns of the cochlea, then the probability of the fulfilment of these expectations is very small, because the edge of the electrode, which is leading during the insertion, will tend to stick like a chisel in the external wall of the cochlea, which as a result will be damaged. During the further insertion it can be difficult to avoid damages to other parts than the external wall, a well since the electrode is prone to curl up with the consequence that it does not reach all the domains aimed at in the cochlea.

Figure 2:
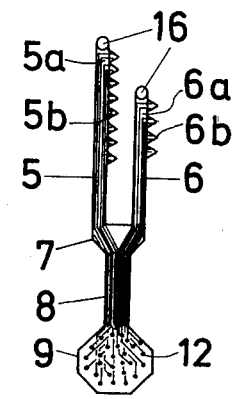
Figure 3:
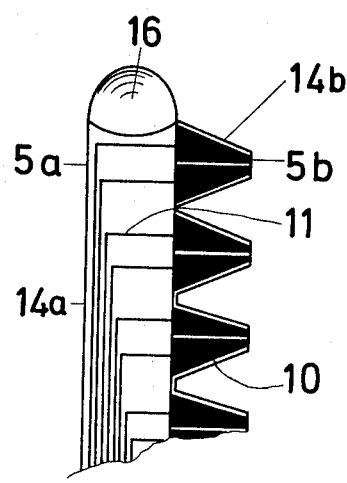

In FIGS. 2 and 3 is illustrated an embodiment of an electrode according to the present invention. It is fork-shaped and comprises two prongs 5 and 6, a shoulder 7, a shank 8 and a socket member 9. Each of the two prongs exhibits in its longitudinal direction a conductor side 5a and 6a respectively and on its opposite side an electrode side 5b and 6b respectively. The electrode side exhibits a number of nerve electrodes 10 illustrated by the solid black trapezoidal areas, each of which being connected to a connecting point 12 on the socket member 9 via an individual conductor 11 situated on the conductor side 5a and 6a respectively.

As the conductors 11 are very thin and are placed very close to each other, it has not been possible to illustrate them in FIG. 2, but a number of them are shown in an enlarged scale in FIGS. 3 illustrating the outermost part of a prong. Here is more clearly showing the outer edge of a supporting foil 14a on the conductor side and 14b on the electrode side, which by means of a suitable application technique, for instance thin film technique, has been provided with conductors, electrodes and socket points. The nerve electrodes 10 are shown arranged in pairs with spacing between adjoining pairs in FIG. 3.

In FIG. 3 is shown a drop-shaped pilot member 16 secured to the insulating support layer. A member of that kind is provided in the extreme end of each prong in order to reduce the inclination to the above mentioned chisel effect during insertion into the cochlea.

Figure 4:
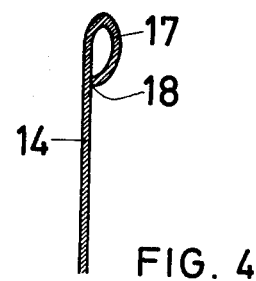

In FIG. 4 is illustrated in a side elevational view a longitudinal section of a prong belonging to another embodiment of the electrode according to the invention. This embodiment is fashioned like that illustrated in FIGS. 2 and 3, but instead of an attached pilot member it has a pilot member which is provided by bending the outermost end 17 of the insulating supporting member to form an eyelet and by fixing it in this position for instance by a heat treatment. A fastening 18 may even be provided in order to stabilize the eyelet in the bevelled position shown relative to the plane of the support foil.

Normally, the two prongs will be manufactured in uneven length because the turns of the cochlea, into which they are to be inserted, are different. The longest one may, as an example, be given eight pairs of electrodes and the shortest one four pairs of electrodes.

The electrode according to the present invention could advantageously be combined with those features, which are described in Danish Pat. No 140,364 and Danish Patent Application Ser. No. 5167/77.

We claim:

1. An implantable flexible electrode for implantation into the cochlea and disposed to establish electrical communication to the auditory nerves of the human ear comprising: an elongated foil-like support member of a flexible electrically insulating material said support member having a planar surface extending along a substantial length thereof and a socket portion at one end thereof; a pattern of electrically conductive paths of a material inert to body fluids and tissue integrally adhered to said planar surface of said support member; a connecting point provided at one end of each of said paths in said socket portion of said support member; one nerve electrode of an array of a plurality of nerve electrodes connected to the opposite end of each of said paths and arranged in an opposite end of said support member; said opposite end of said support member divided into two prongs of uneven lengths each having distal ends and each corresponding to the lengths of particular turns of the cochlea into which said prongs are to be respectively inserted, said nerve electrodes secured to said prongs; and pilot members bevelled with respect to the plane of said foil-like support member attached to said distal ends of said prongs for guiding said prongs through the turns of the cochlea during implantation to thereby reduce damage to the auditory nerves.

2. Am implantable flexible electrode according to claim 1, wherein: said pilot members comprise drop-shaped members secured to each of said prongs.

3. An implantable flexible electrode according to claim 1, wherein: said pilot members comprise eyelets formed in the distal ends of said prongs.

4. An implantable flexible electrode according to claim 1, wherein: a different number of nerve electrodes are secured to each of said prongs.

* * * * *